United States Patent [19]

Poller et al.

[11] 4,115,094
[45] Sep. 19, 1978

[54] ORGANOTIN SUCROSE COMPOUNDS AND METHOD OF USE

[75] Inventors: Robert Clive Poller; Ann Parkin, both of London, England

[73] Assignee: Research Corporation, New York, N.Y.

[21] Appl. No.: 780,053

[22] Filed: Mar. 22, 1977

[51] Int. Cl.² .................. A01N 9/00; C07H 23/00
[52] U.S. Cl. ............................................. 71/88; 71/3; 71/80; 71/84; 71/92; 71/93; 71/97; 424/180; 536/118; 536/119; 536/122
[58] Field of Search ............... 260/429.7; 71/97, 88; 424/180; 536/119, 122

[56] References Cited

U.S. PATENT DOCUMENTS

| 3,459,733 | 8/1969 | Byrd, Jr. et al. ............ 536/119 |
| 3,803,189 | 4/1974 | Haglid ............................ 71/97 |
| 3,894,989 | 7/1975 | Collins et al. ............. 260/429.7 |

*Primary Examiner*—Johnnie R. Brown
*Attorney, Agent, or Firm*—Haight & Huard

[57] ABSTRACT

Organo-tin sucrose compounds wherein three of the tetravalent tin valences are carbon-tin bonds and the fourth is other than a carbon-tin bond exhibit pesticidal and herbicidal activity of the types comparable to the corresponding parent compounds lacking the sucrose residue but with greatly improved water solubility and occasionally higher activity per mole of tin.

27 Claims, No Drawings

ORGANOTIN SUCROSE COMPOUNDS AND METHOD OF USE

BACKGROUND OF THE INVENTION

This invention relates to biocidally active organo-tin sucrose compounds which are carboxylic acid esters of biocidally active organo-tin compounds with sucrose.

A number of biocidally active organo-tin compounds have been developed in recent years for a variety of pesticidal or herbicidal applications, but the practical application thereof is generally limited by their poor water solubility, low vapor pressure or both.

OBJECTS OF THE INVENTION

Accordingly, it is a general object of the present invention to provide organo-tin compounds having pesticidal or herbicidal activity together with improved water solubility.

Another object of this invention is to provide agricultural compositions useful in controlling the growth of undesired plant or animal pests.

A further object of this invention is to provide improved antifouling paints.

An additional object of this invention is to provide a compound, composition and method for controlling mites.

Still another object of this invention is to provide a compound, composition and method for controlling the growth of aquatic weeds.

Upon study of the specification and appended claims, further objects and advantages of this invention will become apparent to those skilled in the art.

SUMMARY OF THE INVENTION

Briefly, the above and other objects, features and advantages of the present invention are attained in one aspect thereof by providing an organo-tin sucrose compound of the formula:

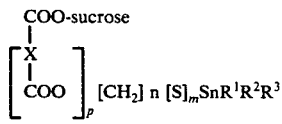

in which the tetravalent tin atom has only three tin-carbon bonds and wherein X is:

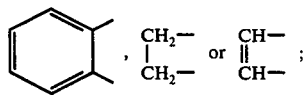

$m$ is 0 or 1;

$p$ is 0 when $m$ is 1 and $p$ is 1 when $m$ is 0;

$n$ is 0 or an integer from 1 to 6 with the proviso that, when $m$ is 1, $n$ is an integer from 1 to 6; and at least two of $R^1$, $R^2$ and $R^3$ are each alkyl of 1 to 8 carbon atoms, cycloalkyl of 3 to 8 carbon atoms or aliphatic aryl or aralkyl of 6 to 10 ring carbon atoms;

when $m$ is 1 or when $m$ and $n$ are both 0, one of $R^1$, $R^2$ and $R^3$ is the acyl radical of an inorganic mineral acid or of a hydrocarbon; carboxylic or sulfonic acid; and when $m$ is 0 or when $m$ is 1 and $n$ is said integer, all of $R^1$, $R^2$ and $R^3$ have the above-indicated values.

DETAILED DISCUSSION

According to this invention there is provided an organo-tin sucrose compound having the general formula:

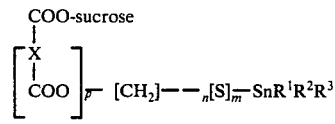

in which sucrose represents a sucrose residue, X represents

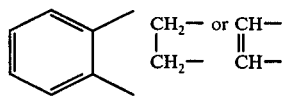

$m$ is 0 or 1, $p$ is 0 when $m$ is 1 and $p$ is 1 when $m$ is 0; $n$ is 0 or an integer from 1 to 6 with the proviso that, when $m$ is 1, $n$ is an integer from 1 to 6; and $R^1$, $R^2$ and $R^3$, which may be the same as or different from one another, are groups such that the tin atom has three tin-carbon bonds and one bond which is not a tin-carbon bond. Thus, in the case when $n$ is 0, $p$ is 1 and $n$ is 0 or in the case where $p$ is 0, $m$ is 1 and $n$ is an integer, $R^1$, $R^2$ and $R^3$ all represent the same or different organic groups so that the tin atom forms its three tin-carbon bonds with carbon atoms of the groups $R^1$, $R^2$ and $R^3$. When $n$ is an integer, $m$ is 0 and $p$ is 1, however, two of $R^1$, $R^2$ and $R^3$ represent organic groups as above and the other $R^1$, $R^2$ and $R^3$ represents an inorganic moiety or an organic moiety, where the organic group is attached to the tin atom by other than a tin-carbon bond.

These organo-tin sucrose compounds have shown biocidal activity. Thus, amongst the compounds of the invention one can find fungicidal, algicidal, miticidal, herbicidal and bactericidal activity. The activities are occasional, per unit weight of tin, higher than the activities of currently used organo-tin compounds. In addition, the presence of a sucrose residue appears to render the compounds more water soluble than many currently used organo-tin compounds.

The organo-tin sucrose compounds of the invention, and in particular those in which $m$ and $n$ are 0, can be prepared in good yields by relatively simple and direct reaction processes. The product is a mixture of compounds which differ in the position of attachment of the oxygen atom to the sucrose residue and in the number of tin-containing groups attached to the sucrose residue. The mixtures can be refined or purified to give a pure product but this is expensive and, since this mixture appears to be biocidally effective, the mixture is usually satisfactory. The use of the single formula:

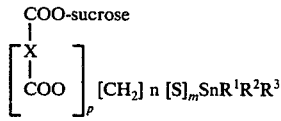

herein is therefore to be construed as embracing the mixtures noted above.

The compounds in which $m$ and $n$ are both zero and $p$ is 1 are preferred since they are usually simpler to prepare and have better bactericidal properties than those in which m is 0, n is an integer from 1 to 6 and p is 1, and so the sucrose residue is directly linked via a tin-carbon bond to the tin atom. When n is an integer and p is 1, it is preferred that n be from 2 to 6 and most preferred that n be 3 or 4, since the intermediates corresponding to the case where n is 3 or 4, and particularly 3, are readily available.

The nature of the groups $R^1$, $R^2$ and $R^3$ is, as noted above, dependent upon the requirement that the tin atom in the organo-tin sucrose compound have three covalent tin-carbon bonds. Organo-tin compounds where there are other than three tin-carbon bonds appear to have less effective biocidal properties.

Those of the groups $R^1$, $R^2$ and $R^3$ which are attached by carbon-tin bonds to the tin atom are organic groups such as alkyl, cycloalkyl groups, aryl and/or alkaryl groups.

The alkyl group is desirably one which contains from 1 to 12 carbon atoms and it may be a straight or branched alkyl group; more preferably, the alkyl group contains 1 to 8 carbon atoms and especially good results seem to be given when the alkyl group contains 4 carbon atoms, e.g. an n-butyl group so that if all three groups $R^1$, $R^2$ and $R^3$ represent alkyl groups, together they contain about 12 carbon atoms which seem to give best results. Suitable alkyl groups include but are not limited to methyl, ethyl, n-propyl, isopropyl, n-butyl, isobutyl, sec.-butyl and tert.-butyl; butyl is preferred. Contemplated alkyl equivalents are alkyl groups bearing one or more substituents, e.g., halogen atoms or lower alkoxy, e.g. methoxyethyl, chloromethyl, methoxybutyl and bromoethyl.

The cylcoalkyl group is desirably one containing from 3 to 8 carbon atoms. Suitable cycloalkyl groups include but are not limited to cyclopropyl, cyclobutyl, cyclopentyl and cyclohexyl, optionally substituted, e.g., by alkyl or alkenyl of up to 4 carbon atoms to form cycloalkylalkyl or cycloalkylalkenyl, e.g., cyclopropylmethyl; cyclohexyl is preferred.

The aryl group is desirably a hydrocarbon aryl group of 6 – 10 ring carbon atoms preferably phenyl or naphthyl and especially phenyl. Aralkyl is aryl substituted by lower alkyl as defined herein, preferably benzyl.

If one of the groups $R^1$, $R^2$ and $R^3$ is attached by other than a tin-carbon bond to the tin atom, that group can be in an inorganic moiety or an organic moiety where the organic portion is linked through other than a carbon atom to the tin atom, i.e. an acyl group.

In the case where one of $R^1$, $R^2$ and $R^3$ represents an inorganic acyl moiety, the acyl group is preferably of an inorganic mineral acid; suitable examples include but are not limited to are halogen atoms such as bromine or chlorine atoms, an inorganic salt group such as a nitrate or phosphate, or one valence of an oxygen or sulphur atom. In the case where one of $R^1$, $R^2$ and $R^3$ represents an organic acyl moiety, the acyl group is preferably of a hydrocarbon carboxylic or sulfonic acid of 1–15 carbon atoms, preferably alkanoyl, aroyl, alkanesulfonyl or arylsulfonyl of 1-8 carbon atoms; suitable examples include but are not limited to the acyl radicals of formic, acetric, propionic and butyric acids; of methane, ethane, propane and butane sulfonic acid; and of benzene, toluene and xylene sulfonic acid. Preferred organic acyl groups are the acetate and p-toluene sulfonate.

These residues $R^1$, $R^2$ and $R^3$ can be unsubstituted or can carry one or two simple substituents, examples of which are lower alkyl groups such as methyl and ethyl groups, halogen atoms such as chlorine atoms, lower alkoxy groups such as methoxy or ethoxy, or amino groups such as dimethylamino groups.

The group X is preferably:

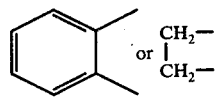

since the compounds in which X is:

while being capable of being made in a fashion similar to compounds where X is

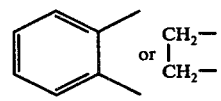

tend to be more difficult to prepare since the products are somewhat oily.

The compounds in which m is 1 and p is 0 can in some circumstances be advantageous in that their synthesis can be relatively simple.

The compounds in which n and m are zero and p is 1, can be prepared by condensing sucrose with an anhydride having the general formula:

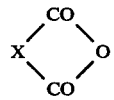

in which X is as defined above to give a sucrose ester of the general formula:

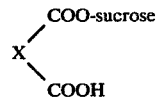

in which X and sucrose are as defined above, followed by reacting the sucrose ester with an organo-tin hydroxide or its corresponding oxide of the general formula:

or

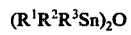

in which $R^1$, $R^2$ and $R^3$ are as defined above. In the first stage of this reaction, the two reagents can be dissolved in an inert, aprotic solvent such as dimethyl formamide, the resulting ester being apparently mixtures including several 1:1 adducts and some 2:1 adducts together with some free sucrose. In the second step of the reaction which involves the use of the expensive organo-tin compound, the reaction proceeds in high yields, often as high as 85%.

To prepare the compounds in which n is an integer, m is 0 and p is 1, the sucrose ester such as sucrose phthalate is initially prepared and then that ester is converted to a metal salt, e.g. the sodium salt which is usually the cheapest and most readily available, and reacted with an organo-tin compound having the general formula:

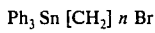

in which n is as defined above and Ph represents a phenyl group, to give a compound of the formula:

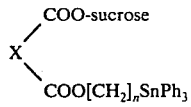

in which X, sucrose, n and Ph are as defined above.

In this compound, the bond between the tin atom and a carbon atom of the aryl (phenyl) group is more sensitive to attack by halogen atoms than the bond between the tin atom and the carbon atom of the linking alkylene group, so that this compound can be converted by reaction with a halogen, such as bromine, in solution in, for example, methyl alcohol, at low temperatures to give the following compound according to the invention:

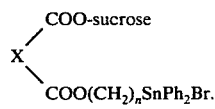

This bromine substituted compound can be hydrolysed, if desired, to eliminate the bromine atom and give the following compound according to the invention:

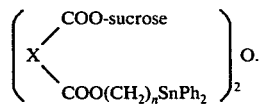

in which X, Ph, sucrose and n are as defined above.

Compounds in which m is 1 and p is 0 can be prepared by reacting an ester having the general formula:

in which $R^1$, $R^2$ and $R^3$ are as defined above, n is 1–6 and R is an alkyl group such as methyl with sucrose.

The reaction can be conducted in a solvent such as dimethylformamide by heating in the presence of an alkali catalyst such as potassium carbonate.

Some organo-tin sucrose compounds of the invention have been found to have good miticidal activity, some to have fungicidal activity, some to have algicidal activity, some to have herbicidal activity and some to have bactericidal activity. The organo-tin sucrose compounds are also safe to use in spraying onto crops either in powder or liquid formulations because when exposed to sunlight or present in soil, the compound is believed to decompose to a safe inorganic tin compound and not to produce long-term pollution.

The biocidally active organo-tin sucrose compounds can be used in essentially the same manner as corresponding prior art compounds lacking the sucrose moiety in the molecule and variations in the non-sucrose portion of the molecule appear to have generally the same effect or biocidal activity as is known for said prior art compounds, e.g. see U.S. Pat. No. 3,264,177 the contents of which are incorporated by reference herein.

Preferred rates for application of the compounds of this invention to foliage, stems and fruit of living plants range from 0.01 to $10^6$ kilograms of active ingredient per hectare. More preferred rates are in the range of 1 to 10,000 kilograms per hectare and the most preferred rates are in the range of 10 to 1,000 kilograms per hectare. The optimum amount within this range depends upon a number of variables which are well known to those skilled in the art of plant protection. These variables include but are not limited to the disease to be controlled, weather conditions expected, the type of crop, stage of development of the crop and the interval between applications. Applications within the range given may need to be repeated one or many more times at intervals of 1 to 60 days.

The compounds of this invention can be applied in a variety of formulations, including wettable powders, dusts, suspensions, emulsifiable concentrates, solutions, granules, pellets, etc. Concentrates can also be prepared for use by formulators in further processing near the point of use. The formulations will include one or more biocidally active compounds of this invention and can include surface-active agents, solid or liquid diluents and other materials as required to produce the desired formulation.

The surface-active agents act as wetting, dispersing and emulsifying agents which assist dispersion of the active material in the spray, and which improve wetting of waxy foliage and the like by the spray. The surfactants can include such anionic, non-ionic and cationic agents as have been used heretofore in similar biocidal compositions. A detailed list of such agents may be found in "Detergents and Emulsifiers Annual," (John W. McCutcheon, Inc.).

Anionic and non-ionic surfactants are preferred. Among the anionic surfactants, preferred ones are alkali and alkaline earth salts of alkylarylsulfonic acids, e.g. decylbenzenesulfonates and alkylnaphthalenesulfonates, dialkyl sodium sulfosuccinate esters, sodium lauryl sulfate, sodium N-methyl-N-oleyltaurate, sodium dodecyldiphenyl ether disulfonate, partial phosphate esters of alkyl and alkylphenyl polyethyleneoxyethanols, and the oleic acid ester of sodium isothionate. Preferred non-ionic surfactants include alkylphenyl polyethylene glycol ethers, polyoxyethylene derivatives of sorbitan fatty esters and long-chain alcohols and mercaptans, as well as polyoxyethylene esters of fatty acids.

Preferred dispersants are alkali and alkaline earth salts of lignosulfonic acids, salts of polymerized alkylarylsulfonates such as are sold under the "Daxad" and "Darvan" trademarks, as well as methylcellulose, polyvinyl alcohol and the like.

Surfactants are present in compositions of this invention in amounts up to about 20% by weight based on the total weight of the resulting composition. When larger amounts of surfactant are desired, as for improved wetting of, spreading on or penetration into foliage, mixing in the spray tank is usually preferable for convenience.

Powder and dust preparations can be made by blending the active ingredient, with or without surfactant, with finely divided solids such as talcs, natural clays, pyrophyllite, diatomaceous earth; flours such as walnut shell, wheat, redwood, soya bean and cotton seed; or inorganic substances such as magnesium carbonate, calcium carbonate, calcium phosphate, sodium silicoaluminate, sulfur and the like. The choice of a particular diluent is based on consideration of the physical and chemical properties required of the product, the chemical and physical properties and concentration of the active ingredient, and the use for which the formulation is intended. The compositions are made by thoroughly blending the active ingredient with the diluent and other additives. Usually a grinding step, as in a hammer mill or fluid energy mill, is included. The particles in dust and powder preparations are preferably less than 50 microns in average diameter. With compounds which are highly water insoluble, improved activity may be obtained with still finer grinding.

Preferred wettable powder formulations will contain 40% or more active ingredient together with sufficient surfactant and inert diluent to permit dispersion in water for spray application. Compositions intended for dust application will generally contain less than 50% active ingredient.

Powdered compositions can be converted to granules by adding a liquid, treating mechanically, and usually drying. Mechanical devices such as granulating pans, mixers and extruders can be used. Compaction devices can be used even without a liquid in the mixture. Water soluble binders, e.g. inorganic salts, urea, ligninsulfonates, methyl cellulose, other water soluble polymers and the like, can be included in these particulate formulations in amounts up to about 25% by weight of the finished granule or pellet. Such materials also aid in disintegration of the pellet and release of the active ingredient under field conditions. Alternatively, a melt, solution or suspension of the active ingredient can be sprayed on the surfact of preformed granules of clay, vermiculite, corn cob and the like. Surfactants may also be included in formulations of the latter type.

Solution formulations can be prepared in suitable solvents. All solution formulations can be used for direct low-volume applications. For such use, all that is required is practical solubility and stability of the active ingredient in the chosen solvent. An important sub-class of solution formulations is emulsifiable concentrates. For these, a water-immisuble solvent is required as well as surfactant to help form and stabilize the final aqueous emulsion in which the biocide is applied. It is preferred that the active ingredient in solution formulations remain totally dissolved at 0° C or as low a storage temperature as can reasonably be expected to occur for prolonged periods. In order to insure this, co-solvents, which may be water-miscible, may also be included in the formulations.

Suspension formulations can be made in water, organic solvents or in mixtures of water and water-miscible organic solvents in which the active ingredient has a solubility under about 0.1%. The preparations usually include, in addition to the active ingredient and liquid carrier, suffacts, viscosity control agents and other modifiers. They are prepared by grinding the components in a sand mill, roller mill or pebble mill, preferably until the average particle size is under 20 microns. It is entirely practical, and in some instances biologically advantageous, to grind until a major proportion of active ingredient is 2 microns in diameter or smaller. Hydrocarbon and other flammable carriers should have boiling points above about 125° C for safety in handling. Suspensions in hydrocarbons are suitable for extension in spray oils and, by inclusion of a suitable emulsifying agent, may also be made sprayable from water.

Organic liquids suitable for preparation of solutions, suspensions and emulsifiable concentrates of the compounds of this invention include alcohols, glycols, Cellosolves, carbitols, ethers, ketones, esters, sulfamides, amides, sulfoxides, sulfones, paraffinic hydrocarbons, aromatic hydrocarbons and halogenated hydrocarbons. Choice of a liquid is dictated by the solubility of the active compound to be used and whether a suspension or solution is desired. The class of compounds represented by the present invention is variable in solubility characteristics, so it is not possible to generalize in the use of particular solvents for particular purposes.

All compositions intended for spray use can contain minor amounts of additives to reduce foam, inhibit corrosion, prevent claying, reduce caking, etc. as the conditions of use may dictate. The conditions of need for an use of such additives are generally known in the art.

The compositions of the invention can contain, in addition to the active ingredient of this invention, conventional insecticides, miticides, bactericides, nematicides, fungicides or other agricultural chemicals such as fruit set agents, fruit thinning compounds, fertilizer ingredients and the like, so that the compositions can serve useful purposes in addition to the biocidal activity of the compounds according to this invention.

Examples of organo-tin sucrose compounds according to the invention are given below in Table 1. Many of these compounds have been tested for their biocidal activities and the results are also given below:

TABLE 1

| COMPOUND | No. |
| --- | --- |
| (n-butyl)$_3$SnOCOC$_6$H$_4$COO-sucrose | 1 |
| (phenyl)$_3$SnOCOC$_6$H$_4$COO-sucrose | 2 |
| (cyclo-C$_6$H$_{11}$)$_3$SnOCOC$_6$H$_4$COO-sucrose | 3 |
| (n-butyl)$_3$SnOCOCH$_2$CH$_2$COO-sucrose | 4 |
| (phenyl)$_3$SnOCOCH$_2$CH$_2$COO-sucrose | 5 |
| sucrose-OCOC$_6$H$_4$COO(CH$_2$)$_3$Sn(phenyl)$_2$Br | 6 |
| (phenyl)$_3$SnSCH$_2$COO - sucrose | 7 |

The compounds were first tested against the fungi which commonly grows on paint coatings, both inside and outside buildings. There are 16 fungi which appear to be most frequently found:

*Alternaria alternata (syn. tenuis);*
*Aspergillus flavus;*
*Aspergillus versicolor;*
Aureobasidium pullulans;
*Cladosporium herbarum;*
*Curvularia geiculata;*
*Dendryphiella salina;*
*Fusarium oxysporum;*
*Paecilomyces variotii;*
*Penicillium expansum;*
*Penicillium purpurogenum;*
*Pestalotia macrotricha;*
*Phoma violacea;*
*Stachybotrys atra;*
*Stemphylium dentriticum;* and
*Trichoderma viride.*

The compounds of the invention were tested for their effectiveness against these 16 fungi by dissolving the compounds in turn in Cellosolve (ethylene glycol monoethyl ether) and incorporating the solution into a CzapekDox agar medium at 100, 10 and 1 ppm by weight. After hardening, the agar plate was inoculated with spore suspensions of the 16 fungi and incubated at 25° C for ten days. Spore germination was then counted; the results are listed in Table 2 together with the results for tributyltin oxide used as a control.

TABLE 2

| Compound | Number of fungi showing inhibition of spore germination (max. 16) | | |
|---|---|---|---|
| | 100 ppm | 10 ppm | 1 ppm |
| 1 | 16 | 16 | 6 |
| 2 | 16 | 14 | 4 |
| 3 | 3 | 0 | 0 |
| 4 | 16 | 16 | 10 |
| 5 | 16 | 15 | 9 |
| 6 | 16 | 7 | 0 |
| 7 | 16 | 11 | 0 |
| tributyltin oxide | 13* | 13 | 12 |

*inactive against

As can be seen from Table 2, most of the compounds show very high activities. The high activity at the 1 ppm level of some of the compounds is remarkable considering the much lower tin content of these compounds compared with standard organo-tin biocides such as the tributyltin oxide.

Compounds 1 and 5 were tested for fungicidal activity in a polyvinyl acetate copolymer emulsion paint having the following composition:
Tioxide RCR . . . 34.2
sodium hexametaphosphate (4% solution) . . . 1.3
Celadol M450 (4% solution) . . . 8.5
water . . . 25.6
Vinamul N6815 . . . 30.4

Various concentrations of the two compounds as well as various concentrations of Amical 48 (a commercial fungicidal) as a control were incorporated into this emulsion paint at the pigment dispersion stage. The emulsions, including a further control emulsion containing no fungicide, were brushed onto plaster covered glass boiling tubes and allowed to dry. One set of painted tubes was tested as made while a second set was tested after 200 hours of artificial weathering according to British Standard BS 3900,F3.

Fungicidal testing was started by inoculating coated tubes with a suspension of mixed fungal spores in 0.01% Tween 80 solution containing not less than $10^4$ spores/ml. The fungal species employed were:

*Alternaria alternata,*
*Aureobasidium pullulans,*
*Cladosporium herbarum,*
*Paecilomyces variotii,*
*Penicillium expansum,* and
*Stemphylium dendriticum.*

Inoculated tubes were kept under conditions designed to promote controlled condensation on paint surfaces and incubated for four weeks. Fungal growth present on painted tubes after this time was assessed by examination through a stereoscopic microscope and rated on a 0-5 scale where 0 = no growth and 5 = overall growth.

In addition, all emulsions were stored for four weeks at 37° C and then examined for color, odor and rheology defects.

All of the emulsions appear to have satisfactory storage properties; no adverse color, odor and rheology changes were apparent after storage. The results of the fungicidal tests are listed in Table 3.

TABLE 3

| Compound | Amount (ppm) | Fungal Growth Assessment | |
|---|---|---|---|
| | | as made | after 200 h. artificial weathering |
| control | none | 4 | 3-4 |
| Amical 48* | 0.25 | 1 | 1 |
| Amical 48 | 0.5 | 0 | 1 |
| Amical 48 | 1.0 | 0 | 0 |
| 5 | 0.25 | 1-2 | 2 |
| 5 | 0.5 | 1-2 | 1-2 |
| 5 | 1.0 | 1 | 1-2 |
| 1 | 0.25 | 2 | 2 |
| 1 | 0.5 | 1-2 | 2 |
| 1 | 1.0 | 1 | 1-2 |

Another established application of organo-tin compounds is in anti-fouling paints; the marine alga Enteromorpha is considered to be mainly involved in the fouling of ships' hulls. Compounds of the invention were tested against Enteromorpha in sea water modified with algal nutrients at concentrations of 1 to 0.1 ppm; the results are listed in Table 4.

TABLE 4

| Compound | Concentration (ppm) | |
|---|---|---|
| | 1 | 0.1 |
| 1 | + | + |
| 2 | + | + |
| 3 | − | − |
| 4 | + | + |
| 5 | + | + |
| 6 | + | + |
| 7 | + | − |

+ = effective
− = not effective

As can be seen from the above, many of the organo-tin sucrose compounds of the invention are remarkably active algicides. For comparative purposes, the minimum concentration at which the commercially used tributyltin oxide and tributyltin fluoride are effective in these tests is 0.3 ppm. The algicidally active sucrose compounds in Table 4 are therefore at least three times more active, even though these sucrose compounds have considerably less than half the tin content of the commercial biocides as shown in Table 5. At a price in early March, 1977 of over $10,000 per ton for tin, the economic savings of higher activity per tin atom can be significant.

TABLE 5

| Compound | % Sn |
|---|---|
| tributyltin oxide | 39.8 |
| tributyltin fluoride | 38.4 |
| $(butyl)_3SnOCOC_6H_4COO$-sucrose | 15.2 |
| $(phenyl)_3SnOCOC_6H_4COO$-sucrose | 14.1 |

Current technology produces anti-fouling paints with prolonged biocidal effectiveness by incorporation of the biocide into a polymer to ensure very slow release of the active material. The poly-functional nature of the sucrose compounds of this invention gives them the ability to be readily incorporated into polymers.

The anti-bactericidal properties of organo-tin sucrose compounds of the invention were tested by growing the bacteria both on agar plates and in a liquid culture; the results are given in Table 6.

TABLE 6

| Compound | Escherichi Coli | | Saccharomyces cerevisiae | | Micrococcus dentifrificans | |
|---|---|---|---|---|---|---|
| | Conc. (ppm) | Inhib. (%) | Conc. (ppm) | Inhib. (%) | Conc. (ppm) | Inhib. (%) |
| 2 | 84 | 100 | 8 | 100 | 0.25 | 100 |

TABLE 6-continued

| Compound | Escherichi Coli Conc. (ppm) | Escherichi Coli Inhib. (%) | Saccharomyces cerevisiae Conc. (ppm) | Saccharomyces cerevisiae Inhib. (%) | Micrococcus dentifrificans Conc. (ppm) | Micrococcus dentifrificans Inhib. (%) |
|---|---|---|---|---|---|---|
| 1 | — | — | — | — | 1 | 100 |
| 6 | 83 | 23 | 8 | 42 | 1 | 100 |

As can be seen above, only very low concentrations of the compounds are required to supress the growth of M.denitrificans. The minimum concentration for inhibition may be even less, since 0.25 ppm was the lowest concentration tested.

Some compounds of the invention, especially compounds 1 and 3, have been found to be effective miticides. They were tested by the leaf dip method as set out in Table 7 and compared with conventional miticides much as Dibrom and Tedion. As can be seen from these results, Compounds 1 and 3 were highly effective.

TABLE 7

| Organism | Compound | Dose (ppm) | Percentage Effectiveness |
|---|---|---|---|
| 2 Spot Mite (Tetranychus urticae Koch) | 3 | 40 | 100 |
|  | 1 | 40 | 100 |
|  | Dibrom | 10 | 39 |
| Mite Eggs (Tetranychus urticae Koch) | 3 | 40 | 100 |
|  | 1 | 40 | 96 |
|  | Tedion | 2.5 | 100 |

Compounds 1, 2 and 3 of the invention were tested for their effect against various weeds and crops both for pre-emergence and post-emergence effects. It was found that compound 3 had no noticeable effect at a dose of about 33 gm cm$^{-2}$; this indicates a lack of phytotoxicity which is important for the use of the compounds as miticide on vegetation. Compounds 1 and 2, on the other hand, were found to have certain selective effects on weeds and crops and so appear useful as selective herbidies. For example, compounds 1 and 2 have no effect on rice, but do have a high degree of toxicity to, for example, wild oats.

Compounds 1 and 2 have also been found to exercise a useful degree of control over the growth of aquatic weeds when present in water at a dose of 2 ppm. They are at least as effective as copper sulphate against aquatic weeds and are also potentially less toxic to aquatic animals, for example, fish, than copper sulphate.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight. The values obtained in elemental analyses are within commonly accepted limited of error. All new products give the expected parent peaks in the mass spectra, and the expected absorption peaks in NMR and IR.

EXAMPLE 1

A. Preparation of phthalic half ester of sucrose

An excess of phthalic anhydride was heated with sucrose in solution in dimethylformamide at a temperature of 60° C for 5 hours. The reaction proceded as in the following reaction scheme:

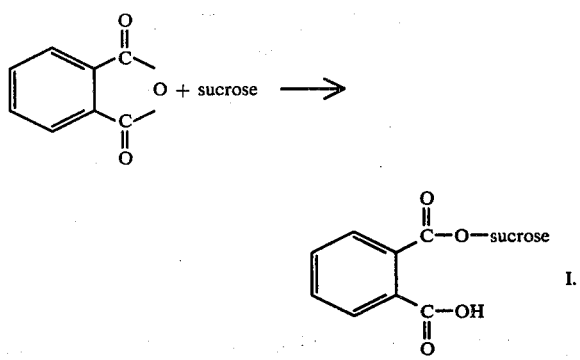

Titration of the resulting ester compound I with standard alkali showed that the ester had the composition of one acid group/molecule.

Analysis: Calculated for 1:1 adduct: C 48.98%; H 5.3%; Found: C 46.6%; H 4.8%

Characteristic features of I.R.

| OH region | 3400 cm$^{-1}$, |
|---|---|
| —C— ‖ O | 1710 cm$^{-1}$. |

B. Preparation of organo-tin compound

The ester I prepared above was reacted with triphenyltin hydroxide or bis(triphenyltin) oxide in solution in benzene at 50° C for 3/4 of an hour to give the compound in a yield of 83% by weight, based on the weight of starting organo-tin compound:

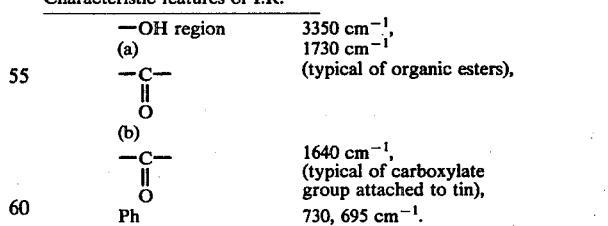

Analysis: Calculated: C 54.4%; H 4.7%; Found: C 54.6%; H 4.8%.

Characteristic features of I.R.

| —OH region (a) | 3350 cm$^{-1}$, 1730 cm$^{-1}$ |
|---|---|
| —C— ‖ O | (typical of organic esters), |
| (b) —C— ‖ O | 1640 cm$^{-1}$, (typical of carboxylate group attached to tin), |
| Ph | 730, 695 cm$^{-1}$. |

EXAMPLE 2

The ester I prepared in part A of Example 1 was reacted with bis(tri-n-butyltin) oxide in solution in benzene at 40° to 50° C for 3/4 of an hour to give the product:

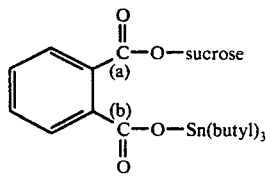

Analysis: Calculated: C 49.29%; H 6.7%; Found: C 50.78%; H 7.00%.

| Characteristic features of I.R. | |
|---|---|
| OH region | 3350 cm$^{-1}$, |
| (a) −C−  ‖  O | 1725 cm$^{-1}$, |
| (b) −C−  ‖  O | 1630 cm$^{-1}$. |

EXAMPLE 3

The phthalic half ester of sucrose prepared as described in part A of Example 1 was treated with sodium hydroxide to give the sodium salt and the latter was reacted with excess $Ph_3Sn(CH_2)_3Br$ in dimethylformamide at 50° C for 3 days to give the compound:

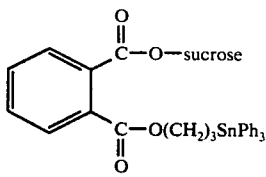

II

Analysis: Calculated: C 54.95%; H 5.2%; Found: C 54.6%; H 5.2%.

| Characteristic features of I.R. | |
|---|---|
| OH region | 3350 cm$^{-1}$, |
| −C−  ‖  O | 1720 cm$^{-1}$. |
| Ph | 925, 690 cm$^{-1}$. |

This compound II was then dissolved in methyl alcohol and reacted at 50° C with bromine to give the compound:

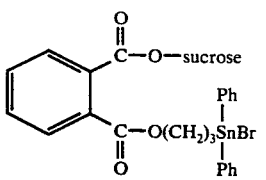

III

Analysis: Calculated: C 47.5%; H 4.64%; Found: C 46.8%; H 5.29%.

| Characteristic features of I.R. | |
|---|---|
| OH region | 3350 cm$^{-1}$. |
| −C−  ‖  O | 1720 cm$^{-1}$. |

| Characteristic features of I.R. | |
|---|---|
| Ph | 730, 695 cm$^{-1}$. |

(Observed reduction in comparative intensity of phenyl absorption to carbonyl absorbtion).

This compound III can be hydrolysed, if so desired, to give the compound:

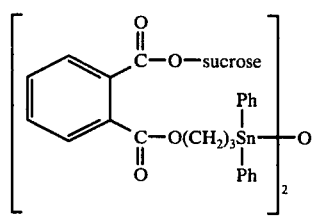

EXAMPLE 4

A. Preparation of succinate half ester of sucrose

This material was prepared in a manner similar to that described in part A of Example 1 for the phthalate half ester, i.e. a 5:1 mixture of succinic anhydride: sucrose was heated at 60° C in dimethyl formamide for 5 hours:

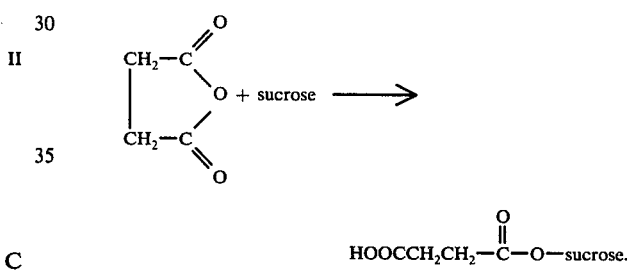

Titration of the product indicated that it had a composition intermediate between a 1:1 and 1:2 structure.

B. Preparation of organotin derivatives of the succinate

The compound:

was prepared using reaction conditions similar to those described for the phthalate derivative, the compound being obtain in a yield of 75% by weight based on the weight of the starting organo-tin compound.

Analysis: Calculated for 1:1 compound: C 46.96%; H 7.10%; Found: C 45.95%; H 7.20%.

Characteristic features of I.R.

C=O at 1730 cm$^{-1}$ 1640 cm$^{-1}$
OH 3400 cm$^{-1}$

EXAMPLE 5

In a similar manner, the compound:

was prepared in a yield of 84%.

Analysis $C_{34}H_{40}O_{14}Sn$: Calculated: C 51.6%; H 5.1%; Found: C 51.4%; H 4.7%.

Characteristic features of I.R.

C=O 1730 cm$^{-1}$, 1640 cm$^{-1}$
OH 3400 cm$^{-1}$
Ph 690 cm$^{-1}$, 730 cm$^{-1}$.

EXAMPLE 6

Other Derivatives of Phthalate Half Ester

In a similar manner, the tricyclohexyl tin derivative:

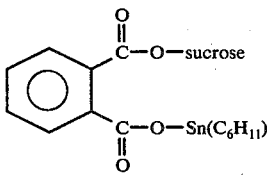

was prepared in a yield of 80%.

Analysis $C_{38}H_{58}O_{14}Sn$: Calculated: C 53.2%; H 6.6%; Found: C 53.1%; H 6.6%.

Characteristic features of I.R.

C=O at 1730 cm$^{-1}$, 1640 cm$^{-1}$
OH at 3400 cm$^{-1}$.

EXAMPLE 7

Methyl-S-triphenylstannylthioglycollate (2.0 g, 4.4 mmole) was dissolved in 15 ml dimethylformamide and heated with sucrose (4.5 g, 13.2 mmole) in 45 ml dimethylformamide and potassium carbonate (0.04 g) at 50°–55° C for two hours.

The solution was poured into cyclohexane and the lower layer washed with several portions of cyclohexane until the majority of the dimethylformamide had been removed. The resulting semi-solid was extracted with chloroform and the solvent removed. The purification procedure (cyclohexane wash, chloroform extraction) was repeated to leave 1.2 g solid which was found to consist of some unreacted sucrose and a mixture of substituted products.

Analysis $C_{32}H_{58}O_{12}SSn$: Calculated: C 50.20%; H 4.97%; Found: C 51.42%; H 5.58%.

The preceding examples can be repeated with similar success by substituting the generically or specifically described components and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An organo-tin sucrose compound of the formula:

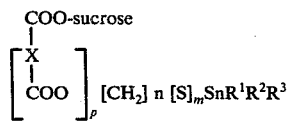

in which the tetravalent tin atom has only three tin-carbon bonds and wherein X is:

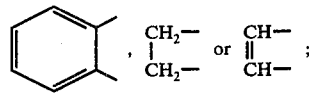

m is 0 or 1;
p is 0 when m is 1 and p is 1 when m is 0;
n is 0 or an integer from 1 to 6 with the proviso that, when m is 1, n is an integer from 1 to 6; and
at least two of $R^1$, $R^2$ and $R^3$ are each alkyl of 1 to 8 carbon atoms, cycloalkyl of 3 to 8 carbon atoms or hydrocarbon aryl or aralkyl of 6 to 10 ring carbon atoms;
when m is 1 or when m and n are both 0, one of $R^1$, $R^2$ and $R^3$ is the acyl radical of an inorganic mineral acid or of a hydrocarbon carboxylic or sulfonic acid of 1–15 carbon atoms; and
when m is 0 or when m is 1 and n is said integer, all of $R^1$, $R^2$ and $R^3$ have the above-indicated values.

2. A compound according to claim 1, wherein m = 0 and p = 1.

3. A compound according to claim 2, wherein n is 0 or an integer from 2 to 6.

4. A compound according to claim 3, wherein n is 3 or 4.

5. A compound according to claim 3, wherein n is 0.

6. A compound according to claim 1, wherein alkyl is butyl.

7. A compound according to claim 1, wherein cycloalkyl is cyclohexyl.

8. A compound according to claim 1, wherein hydrocarbon aryl is phenyl.

9. A compound according to claim 1, wherein hydrocarbon aralkyl is benzyl.

10. A compound according to claim 1, wherein at least two of $R^1$, $R^2$ and $R^3$ have the same values.

11. A compound according to claim 10, wherein $R^1 = R^2 = R^3$.

12. A compound according to claim 1, wherein one of $R^1$, $R^2$ and $R^3$ is the acyl radical of an inorganic mineral acid.

13. A compound according to claim 1, wherein one of $R^1$, $R^2$ and $R^3$ is the acyl radical of a hydrocarbon carboxylic or sulfonic acid of 1 to 8 carbon atoms.

14. A compound according to claim 13, wherein said acyl radical is p-toluene sulfonate.

15. A compound according to claim 1, (n-butyl)$_3$SnOCOC$_6$H$_4$COO-sucrose.

16. A compound according to claim 1, (phenyl)$_3$SnOCOC$_6$H$_4$COO-sucrose.

17. A compound according to claim 1, (cyclo-C$_6$H$_{11}$)$_3$SnOCOC$_6$H$_4$COO-sucrose.

18. A compound according to claim 1, (n-butyl)$_3$SnOCOCH$_2$CH$_2$COO-sucrose.

19. A compound according to claim 1, (phenyl)$_3$SnOCOCH$_2$CH$_2$COO-sucrose.

20. A compound according to claim 1, sucrose-OCOC$_6$H$_4$COO(CH$_2$)$_3$Sn(phenyl)$_2$Br.

21. A compound according to claim 1, (phenyl)$_3$SnSCH$_2$COO-sucrose.

22. A pesticidal composition suitable for treating pesticidal infestations of living plants, comprising a pesticidally effective amount of a compound according to claim 1 in combination with an agriculturally acceptable carrier.

23. A method of inhibiting the growth of plant pests which comprises contacting them with a lethal amount of a compound according to claim 1.

24. A method according to claim 23 wherein said pest is a mite.

25. A method according to claim 24 wherein said compound is one in which $R^1$, $R^2$ and $R^3$ are each cyclohexyl.

26. A method according to claim 25 wherein said compound is (cyclo-$C_6H_{11}$)$_3$SNOCOC$_6$H$_4$COO-sucrose.

27. A composition according to claim 27 wherein said compound is (cyclo-$C_6H_{11}$)$_3$SNOCOC$_6$H$_4$COO-sucrose.

* * * * *